(12) United States Patent
Evans et al.

(10) Patent No.: US 7,741,032 B2
(45) Date of Patent: Jun. 22, 2010

(54) GENOTYPING ASSAY TO PREDICT GAMMA GLUTAMYL HYDROLASE (GGH) ACTIVITY

(75) Inventors: William Edward Evans, Cordova, TN (US); Mary Relling, Cordova, TN (US); Qing Cheng, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 751 days.

(21) Appl. No.: 10/887,002

(22) Filed: Jul. 8, 2004

(65) Prior Publication Data

US 2006/0008811 A1    Jan. 12, 2006

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search ................ None
See application file for complete search history.

(56) References Cited

U.S. PATENT DOCUMENTS

2003/0092019 A1* 5/2003 Meyer et al. .............. 435/6
2006/0057609 A1  3/2006 Dervieux

OTHER PUBLICATIONS

Chave et al. (Gene, vol. 319, pp. 167-175, Nov. 13, 2003).*
Cheng et al. (Pharmacogentics, vol. 14, pp. 557-567, Aug. 2004).*
Yao et al. (PNAS, vol. 93, pp. 10134-10138, Sep. 1996).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Cheng et al. (Am. J. Hum. Genetics. vol. 79, pp. 264-274, 2006).*
Brenner, T., et al., "Pharmacogenomics of childhood acute lymphoblastic leukemia" *Curr Opin Mol Ther 6*: 567-578 (2002).
Chave, K.J. et al., "Molecular modelingand sie-directed mutagenesis define the catalytic motif in human Gamma-glutamyl hudrolase" *J. Biol Chem 275*: 40365-40370 (2000).
Chave, K.J. et al., "Identification of single nucleotide polymorphisms in the human gamma-glutamyl hydrolase gene and characterization of promoter polymorphisms", *Gene 319*: 167-175 (2003).
Cheng, Q. et al., "A substrate specific functional polymorphism of human Y- glutamyl hydrolase alters catalytic activity and methotrexate polyglutamate accumulation in acute lymphoblastic leukaemia cells" *Pharmacogenetics 14*: 557-567 (2004).
Evans, W.E., et al., "Pharmacogenomics—drug disposition, drug targets, and side effects", *N. Engl J Med 348*: 538-549 (2003).
Evans, W.E., et al., "Pharmacogenomics: translating functional genomics into national therapeutics", *Science 286*: 487-491 (1999).
Evans, W.E., et al., "Conventional compared with individualized chemotherapy for childhood acute lymphoblastic leukemia". *N. Engl J Med 338*: 499-505 (1998).
Galivan, J., et al., "Glutamyl hydrolase properties and pharmacologic impact", *Semin Oncol 28*: 33-37 (1999).
Li, H. et al., "Three-dimensional structure of human gamma-glutamyl hydrolase. A class I glatamine amidotransferase adapted for a complex and site-directed mutagenesis define the catalytic motif in Human gamma-glytamyl hydrolase" *J Biol Chem 277*: 24522-24527 (2002).
Panetta, J.C., et al., "Methotrexate Intracellular disposition in acute lymphoblastic leukemia: a mathematical model of gamma-glutamyl hydrolase activity", *Clin Cancer Res 8*: 2423-2429 (2002).
Pui, C.H., et al., "Results of therapy for acute lymphoblastic leukemia in black and which children", *JAMA 290*: 2001-2007 (2003).
Rhee, M.S., et al., Characterization of human cellular gamma-glutamyl hydrolase. *Mol Pharmacol 53*: 1040-1046 (1998).
Yao, R., et al., "Human gamma-glutamyl hydrolase: cloning and characterization of the enzyme expressed in vitro", *Proc Natl Acad Sci USA 83*: 10134-10138 (1996).
Yin, D. et al., "Structural organization of the human gamma-glutamyl hudrolase gene" *Gene 238*:463-470 (1999).

* cited by examiner

*Primary Examiner*—Jeanine A Goldberg
(74) *Attorney, Agent, or Firm*—Licata & Tyrrell P.C.

(57) ABSTRACT

Single nucleotide polymorphisms (SNPs) in the gene encoding gamma glutamyl hydrolase (GGH) associated with reduced GGH activity are disclosed. The primary SNP is a change from a cytosine to a thymine at a position corresponding to nucleotide 511 of Genbank sequence accession no. NM 003878. Methods and kits for detecting these SNPs are provided, along with primers useful in detecting these SNP and for amplifying portions of the GGH gene containing these SNPs.

4 Claims, 1 Drawing Sheet

FIGURE 1

Genotype and allele frequencies of 452C>T(T127I) GGH in different ALL subtypes

| Sub-type ALL | GGH activity | Sample (n) | Allele (n) | Ile127 n | % allele | 95% CI |
|---|---|---|---|---|---|---|
| non-hyperdiploid B-lineage ALL | Low | 10 | 20 | 4 | 20.0 | 2.5 – 37.5 |
| | Med | 18 | 36 | 4 | 11.1 | 0.8 – 21.4 |
| | High | 10 | 20 | 0 | 0 | |
| hyperdiploid B-lineage ALL | Low | 3 | 6 | 1 | 16.7 | 0 – 46.5 |
| | Med | 6 | 12 | 1 | 8.3 | 0 – 24.0 |
| | High | 3 | 6 | 0 | 0 | |
| T-lineage ALL | Low | 4 | 8 | 1 | 12.5 | 0 – 35.4 |
| | Med | 8 | 16 | 1 | 6.3 | 0 – 18.1 |
| | High | 4 | 8 | 0 | 0 | |
| | GGH activity | Sample (n) | Allele (n) | Ile127 n | % allele | 95% CI |
| Total ALL patients studied | Low | 17 | 34 | 6 | 17.6 | 4.8 – 30.5 |
| | Med | 32 | 64 | 6 | 9.4 | 2.2 – 16.5 |
| | High | 17 | 34 | 0 | 0 | |

SEQUENCE LISTING

<160> NUMBER OF SEQ ID NOS: 8

<210> SEQ ID NO 1
<211> LENGTH: 1280
<212> TYPE: DNA
<213> ORGANISM: Homo sapiens
<220> FEATURE:
<221> NAME/KEY: CDS
<222> LOCATION: (60)..(1016)

<400> SEQUENCE: 1

```
tgccgcagcc cccgcccgcc cgcagagctt ttgaaaggcg gcgggaggcg gcgagcgcc          59 atg gcc agt ccg ggc tgc ctg ctg tgc gtg ctg ggc ctg cta ctc tgc         107
Met Ala Ser Pro Gly Cys Leu Leu Cys Val Leu Gly Leu Leu Leu Cys
1               5                   10                  15 ggg gcg gcg agc ctc gag ctg tct aga ccc cac ggc gac acc gcc aag         155
Gly Ala Ala Ser Leu Glu Leu Ser Arg Pro His Gly Asp Thr Ala Lys
                20                  25                  30 aag ccc atc atc gga ata tta atg caa aaa tgc cgt aat aaa gtc atg         203
Lys Pro Ile Ile Gly Ile Leu Met Gln Lys Cys Arg Asn Lys Val Met
            35                  40                  45 aaa aac tat gga aga tac tat att gct gcg tcc tat gta aag tac ttg         251
Lys Asn Tyr Gly Arg Tyr Tyr Ile Ala Ala Ser Tyr Val Lys Tyr Leu
        50                  55                  60 gag tct gca ggt gcg aga gtt gta cca gta agg ctg gat ctt aca gag         299
Glu Ser Ala Gly Ala Arg Val Val Pro Val Arg Leu Asp Leu Thr Glu
65                  70                  75                  80 aaa gac tat gaa ata ctt ttc aaa tct att aat gga atc ctt ttc cct         347
Lys Asp Tyr Glu Ile Leu Phe Lys Ser Ile Asn Gly Ile Leu Phe Pro
                85                  90                  95 gga gga agt gtt gac ctc aga cgc tca gat tat gct aaa gtg gcc aaa         395
Gly Gly Ser Val Asp Leu Arg Arg Ser Asp Tyr Ala Lys Val Ala Lys
                100                 105                 110 ata ttt tat aac ttg tcc ata cag agt ttt gat gat gga gac tat ttt         443
Ile Phe Tyr Asn Leu Ser Ile Gln Ser Phe Asp Asp Gly Asp Tyr Phe
            115                 120                 125 cct gtg tgg ggc aca tgc ctt gga ttt gaa gag ctt tca ctg ctg att         491
Pro Val Trp Gly Thr Cys Leu Gly Phe Glu Glu Leu Ser Leu Leu Ile
        130                 135                 140 agt gga gag tgc tta tta act gcc aca gat act gtt gac gtg gca atg         539
Ser Gly Glu Cys Leu Leu Thr Ala Thr Asp Thr Val Asp Val Ala Met
145                 150                 155                 160 ccg ctg aac ttc act gga ggt caa ttg cac agc aga atg ttc cag aat         587
Pro Leu Asn Phe Thr Gly Gly Gln Leu His Ser Arg Met Phe Gln Asn
                165                 170                 175 ttt cct act gag ttg ttg ctg tca tta gca gta gaa cct ctg act gcc         635
Phe Pro Thr Glu Leu Leu Leu Ser Leu Ala Val Glu Pro Leu Thr Ala
                180                 185                 190 aat ttc cat aag tgg agc ctc tcc gtg aag aat ttt aca atg aat gaa         683
Asn Phe His Lys Trp Ser Leu Ser Val Lys Asn Phe Thr Met Asn Glu
            195                 200                 205 aag tta aag aag ttt ttc aat gtc tta act aca aat aca gat ggc aag         731
Lys Leu Lys Lys Phe Phe Asn Val Leu Thr Thr Asn Thr Asp Gly Lys
        210                 215                 220 att gag ttt att tca aca atg gaa gga tat aag tat cca gta tat ggt         779
Ile Glu Phe Ile Ser Thr Met Glu Gly Tyr Lys Tyr Pro Val Tyr Gly
225                 230                 235                 240 gtc cag tgg cat cca gag aaa gca cct tat gag tgg aag aat ttg gat         827
Val Gln Trp His Pro Glu Lys Ala Pro Tyr Glu Trp Lys Asn Leu Asp
```

-continued

```
                 245                 250                 255
ggc att tcc cat gca cct aat gct gtg aaa acc gca ttt tat tta gca      875
Gly Ile Ser His Ala Pro Asn Ala Val Lys Thr Ala Phe Tyr Leu Ala
            260                 265                 270 gag ttt ttt gtt aat gaa gct cgg aaa aac aac cat cat ttt aaa tct      923
Glu Phe Phe Val Asn Glu Ala Arg Lys Asn Asn His His Phe Lys Ser
        275                 280                 285 gaa tct gaa gag gag aaa gca ttg att tat cag ttc agt cca att tat      971
Glu Ser Glu Glu Glu Lys Ala Leu Ile Tyr Gln Phe Ser Pro Ile Tyr
290                 295                 300 act gga aat att tct tca ttt cag caa tgt tac ata ttt gat tga         1016
Thr Gly Asn Ile Ser Ser Phe Gln Gln Cys Tyr Ile Phe Asp
305                 310                 315 aagtcttcaa tttgttaaca gagcaaattt gaataattcc atgattaaac tgttagaata   1076
acttgctact catggcaaga ttaggaagtc acagattctt ttctataatg tgcctggctc   1136
tgattcttca ttatgtatgt gactatttat ataacattag ataattaaat agtgagacat   1196
aaatagagtg cttttcatg gaaaagcctt cttatatctg aagattgaaa ataaattta    1256 ctgaaataca aaaaaaaaaa aaaa                                          1280
```

<210> SEQ ID NO 2
<211> LENGTH: 318
<212> TYPE: PRT
<213> ORGANISM: Homo sapiens

<400> SEQUENCE: 2

```
Met Ala Ser Pro Gly Cys Leu Leu Cys Val Leu Gly Leu Leu Leu Cys
1               5                   10                  15

Gly Ala Ala Ser Leu Glu Leu Ser Arg Pro His Gly Asp Thr Ala Lys
            20                  25                  30

Lys Pro Ile Ile Gly Ile Leu Met Gln Lys Cys Arg Asn Lys Val Met
        35                  40                  45

Lys Asn Tyr Gly Arg Tyr Tyr Ile Ala Ala Ser Tyr Val Lys Tyr Leu
    50                  55                  60

Glu Ser Ala Gly Ala Arg Val Val Pro Val Arg Leu Asp Leu Thr Glu
65                  70                  75                  80

Lys Asp Tyr Glu Ile Leu Phe Lys Ser Ile Asn Gly Ile Leu Phe Pro
                85                  90                  95

Gly Gly Ser Val Asp Leu Arg Arg Ser Asp Tyr Ala Lys Val Ala Lys
            100                 105                 110

Ile Phe Tyr Asn Leu Ser Ile Gln Ser Phe Asp Asp Gly Asp Tyr Phe
        115                 120                 125

Pro Val Trp Gly Thr Cys Leu Gly Phe Glu Glu Leu Ser Leu Leu Ile
    130                 135                 140

Ser Gly Glu Cys Leu Leu Thr Ala Thr Asp Thr Val Asp Val Ala Met
145                 150                 155                 160

Pro Leu Asn Phe Thr Gly Gly Gln Leu His Ser Arg Met Phe Gln Asn
                165                 170                 175

Phe Pro Thr Glu Leu Leu Leu Ser Leu Ala Val Glu Pro Leu Thr Ala
            180                 185                 190

Asn Phe His Lys Trp Ser Leu Ser Val Lys Asn Phe Thr Met Asn Glu
        195                 200                 205

Lys Leu Lys Lys Phe Phe Asn Val Leu Thr Thr Asn Thr Asp Gly Lys
    210                 215                 220

Ile Glu Phe Ile Ser Thr Met Glu Gly Tyr Lys Tyr Pro Val Tyr Gly
```

-continued

```
            225                 230                 235                 240

Val Gln Trp His Pro Glu Lys Ala Pro Tyr Glu Trp Lys Asn Leu Asp
                245                 250                 255

Gly Ile Ser His Ala Pro Asn Ala Val Lys Thr Ala Phe Tyr Leu Ala
                260                 265                 270

Glu Phe Phe Val Asn Glu Ala Arg Lys Asn Asn His Phe Lys Ser
                275                 280                 285

Glu Ser Glu Glu Glu Lys Ala Leu Ile Tyr Gln Phe Ser Pro Ile Tyr
                290                 295                 300

Thr Gly Asn Ile Ser Ser Phe Gln Gln Cys Tyr Ile Phe Asp
305                 310                 315

<210> SEQ ID NO 3
<211> LENGTH: 25
<212> TYPE: DNA
<213> ORGANISM: Homo sapiens

<400> SEQUENCE: 3
tgttttctgt gtgtgtatgg gtcgg                                                25

<210> SEQ ID NO 4
<211> LENGTH: 25
<212> TYPE: DNA
<213> ORGANISM: Homo sapiens
<220> FEATURE:
<221> NAME/KEY: misc_feature
<223> OTHER INFORMATION: Oligo

<400> SEQUENCE: 4
tgctacttac taatcctgcc cagca                                                25

<210> SEQ ID NO 5
<211> LENGTH: 22
<212> TYPE: DNA
<213> ORGANISM: Homo sapiens
<220> FEATURE:
<221> NAME/KEY: misc_feature
<223> OTHER INFORMATION: Oligo

<400> SEQUENCE: 5
tgttttccag cctgtgtggg ag                                                   22

<210> SEQ ID NO 6
<211> LENGTH: 24
<212> TYPE: DNA
<213> ORGANISM: Homo sapiens
<220> FEATURE:
<221> NAME/KEY: misc_feature
<223> OTHER INFORMATION: Oligo

<400> SEQUENCE: 6
ggatggtcat tcacatcttc aacc                                                 24

<210> SEQ ID NO 7
<211> LENGTH: 38
<212> TYPE: DNA
<213> ORGANISM: Homo sapiens
```

```
<400> SEQUENCE: 7
gtggagagtg cttattaatt gccacagata ctgttgac                          38

<210> SEQ ID NO 8
<211> LENGTH: 38
<212> TYPE: DNA
<213> ORGANISM: Homo sapiens

<400> SEQUENCE: 8
gtcaacagta tctgtggcaa ttaataagca ctctccac                          38
```

GENOTYPING ASSAY TO PREDICT GAMMA GLUTAMYL HYDROLASE (GGH) ACTIVITY

GOVERNMENT INTEREST

This invention was made in part with U.S. Government support under National Institutes of Health grant nos. CA36401, CA78224, CA51001, and GM61393. The U.S. Government may have certain rights in this invention.

FIELD OF THE INVENTION

This invention relates generally to the field of diagnostics based on the detection of DNA sequence polymorphisms.

BACKGROUND

Methotrexate (MTX) is an antifolate that is used essentially in all treatment protocols for childhood acute lymphoblastic leukemia (ALL). After its entry into cells, MTX is rapidly converted to γ-glutamyl polyglutamates through the action of folypolyglutamate synthetase (FPGS). Long chain polyglutamates ($MTXPG_{4-7}$) are more avid inhibitors of folate-dependent enzymes and are also retained longer within cells, thereby increasing and prolonging MTX's antifolate effects. Higher accumulation of MTXPG has been associated with increased cytotoxicity and treatment response in childhood ALL.

Significant lineage and ploidy differences have been observed in MTX-PG accumulation in ALL cells, with T-lineage ALL having the lowest MTX-PG accumulation and hyperdiploid (>50 chromosomes) and B-lineage ALL having the highest MTX-PG accumulation. The underlying mechanisms for these differences include lower FPGS activity in T-ALL. However, following uniform treatment with HDMTX, there remain substantial inter-individual differences in MTX-PG accumulation within each of the three lineage and ploidy subtypes of ALL, for reasons that have not been fully elucidated.

One potential cause of inter-individual differences in MTX-PG accumulation is heterogeneity in γ-Glutamyl hydrolase (GGH, also known as folypolyglutamate hydrolase, FPGH, EC 3.4.19.9), a lysosomal peptidase that catalyzes the removal of γ-linked polyglutamates, converting long-chain MTX-PG into shorter-chain MTX-PG and ultimately to MTX. This allows MTX to be effluxed from cells and thereby reduces the overall effectiveness of MTX. The human GGH gene spans 24 kb on chromosome 8 (q12.23-13.1) and comprises nine exons (Yin, D. et al., "Structural organization of the human gamma-glutamyl hydrolase gene" *Gene* 238: 463-470 (1999)). The crystal structure of human GGH has been determined and a model for substrate recognition and hydrolysis has been proposed (Li, H. et al., "Three-dimensional structure of human gamma-glutamyl hydrolase. A class I glatamine amidotransferase adapted for a complex substate" *J Biol Chem* 277: 24522-24529 (2002); Chave, K. J, et al., "Molecular modeling and site-directed mutagenesis define the catalytic motif in human gamma-glutamyl hydrolase" *J Biol Chem* 275: 40365-40370 (2000)). Cellular GGH is predominantly lysosomal, with an acidic pH optimum, functioning as either an endopeptidase or exopeptidase, exhibiting species differences in these functions. Human GGH has a higher affinity for the longer chain MTX polyglutamates, cleaving multiple glutamyl residues, having its highest activity at the outermost or two outermost residues in the polyglutamate chain (Panetta, J. C., et al., id).

Polymorphisms within the GGH gene have been reported (Chave, K. J. et al., "Identification of single nucleotide polymorphisms in the human gamma-glutamyl hydrolase gene and characterization of promoter polymorphisms". *Gene* 319: 167-175 (2003)). These polymorphisms which occurred in the promoter region of the GGH gene were reported as potentially affecting expression of the GGH protein, while a polymorphism occurring in the coding region which caused a codon change (452 C>T; T127I) was reported as not changing GGH activity (Chave, K. J. et al., 2003, id). This report indicates that GGH promoter polymorphisms may play a role in inter-individual differences in MTX-PG accumulation, but that the coding region polymorphism does not since it did not change GGH activity.

SUMMARY OF THE INVENTION

The present invention relates to the association of a point mutation or single nucleotide polymorphism (SNP) in an exon of the gamma glutamyl hydrolase (GGH) gene which causes a substitution in the amino acid sequence of GGH. The presence of this mutant allele is directly correlated with lower levels of GGH activity.

This polymorphism occurs at a position in exon 5 of the human GGH gene that corresponds to nucleotide 511 of Genbank sequence accession no. NM 003878 (position 511 of SEQ ID No. 1). In the wildtype GGH gene the nucleotide at this position is a cytosine and is part of the three nucleotide codon ACT which encodes a threonine (THR) in the GGH protein. The mutation identified herein associated with lower levels of GGH activity is a change in the nucleotide at this position to a thymine, which changes the corresponding codon to ATT which encodes an isoleucine (ILE) in the mutant GGH protein.

The present invention includes a method for determining the gamma glutamyl hydrolase (GGH) genotype of an individual with respect to this mutation. A method for predicting the level of gamma glutamyl hydrolase (GGH) activity in a subject based on the presence or absence of this mutation on one or both alleles is also provided.

In another aspect a kit useful for performing these methods is provide. In yet another aspect, hybridisation primers at least 10 nucleotides long corresponding to a portion of the GGH gene containing this SNP are provided. In yet another aspect, polynucleotide primers at least 10 nucleotides long useful in amplifying the portion of the GGH gene containing this SNP via polymerase chain reaction (PCR) or similar means.

In addition to the primary SNP associated with low GGH activity, two additional SNPs within the GGH gene associated with low GGH activity are provided. One of these SNPs occurs in exon 2 of the human GGH gene at a position corresponding to nucleotide 233 of Genbank sequence accession no. NM 003878 (position 233 of SEQ ID No. 1) and involves a change from a guanine to an adenine. The other SNP identified by the inventors as associated with low GGH activity occurs in the 3' untranslated region of the GGH gene at a position corresponding to nucleotide 1161 of Genbank sequence accession no. NM 003878 (position 1161 of SEQ ID No. 1) and involves a change from an adenine to a guanine. The present invention also extends to diagnostic assays, kits and methods for determining the gamma glutamyl hydrolase (GGH) genotype of a subject with respect to these two additional SNPs.

DESCRIPION OF THE FIGURE

FIG. 1 correlates the level of gamma glutamyl hydrolase (GGH) activity in patients with various subtypes of acute lymphoblastic leukemia (ALL) with the presence of a mutated GGH allele (cytosine to thymine) at the position corresponding to position 511 of SEQ ID No. 1. For the entire group of ALL patients studied (n=66), there was a significant difference in frequency of the mutated GGH allele among patients with low, intermediate and high GGH activity (p=0.025 by Exact chi square test).

DESCRIPTION OF THE SEQUENCE LISTING

SEQ ID No. 1 is a reproduction of the human gamma glutamyl hydrolase (GGH) gene sequence deposited as Genbank sequence accession no. NM 003878. For purposes of this invention, the critical nucleotide is the cytosine located at position 511 and underlined in the following reproduction of nucleotides 500-520 from SEQ ID No. 1: (GTGCTTATTAA CTGCCACAGA). The mutation identified herein associated with lower levels of GGH activity is a change from a cytosine (C) to a thymine (T) at this position.

SEQ ID No. 2 is the amino acid sequence of the human GGH protein encoded by the coding portion of SEQ ID No. 1 (i.e. from nucleotide 60 to nucleotide 1013 of SEQ ID No.1).

SEQ ID No. 3 is an oligonucleotide having the sequence TGTTTTCTGTGTGTGTATGGGTCGG designed for use with SEQ ID No. 4 as a forward primer for amplifying a portion of the GGH gene containing the polymorphism that corresponds to nucleotide 511 of Genbank sequence accession no. NM 003878 (position 511 of SEQ ID No. 1).

SEQ ID No. 4 is an oligonucleotide having the sequence TGCTACTTACTAATCCTGCCCAGCA designed for use with SEQ ID No.3 as a reverse primer for amplifying a portion of the GGH gene containing the polymorphism that corresponds to nucleotide 511 of Genbank sequence accession no. NM 003878 (position 511 of SEQ ID No. 1).

SEQ ID No. 5 is an oligonucleotide having the sequence TGTTTTCCAGCCTGTGTGGGAG designed for use with SEQ ID No. 6 as a forward primer for amplifying a portion of the GGH gene containing the polymorphism that corresponds to nucleotide 511 of Genbank sequence accession no. NM 003878 (position 511 of SEQ ID No. 1).

SEQ ID No. 6 is an oligonucleotide having the sequence GGATGGTCATTCACATCTTCAACC designed for use with SEQ ID No.5 as a reverse primer for amplifying a portion of the GGH gene containing the polymorphism that corresponds to nucleotide 511 of Genbank sequence accession no. NM 003878 (position 511 of SEQ ID No. 1).

SEQ ID No. 7 is an oligonuclotide having the sequence GTGGAGAGTGCTTATTAA TTGCCACAGATACTGTTGAC designed for use with SEQ ID No. 8 as a forward primer for mutagenizing the GGH gene at the position corresponding to nucleotide 511 of Genbank sequence accession no. NM 003878 (position 511 of SEQ ID No. 1; see underlined nuclotide). This oligonucleotide can also be used to determine the identity of the nucleotide at this position of the GGH gene in a DNA sample.

SEQ ID No. 8 is an oligonuclotide having the sequence GTCAACAGTATCTGTGGCA ATTAATAAGCACTCTCCAC designed for use with SEQ ID No. 7 as a reverse primer for mutagenizing the GGH gene at the position corresponding to nucleotide 511 of Genbank sequence accession no. NM 003878 (position 511 of SEQ ID No. 1; see underlined nuclotide). This oligonucleotide can also be used to determine the identity of the nucleotide at this position of the GGH gene in a DNA sample.

DETAILED DESCRIPTION OF THE INVENTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Definitions: The terms and phrases used herein to describe and claim the present invention shall have the meanings set forth below.

By "oligonucleotide," is meant a molecule comprised of two or more ribonucleotides, preferably more than three. Its exact size will depend upon many factors which, in turn, depend upon the ultimate function and use of the oligonucleotide. The oligonucleotides of the invention useful as primers or hybridization probes are preferably from 10 to 50 nucleotides in length, even more preferably from 20-30 nucleotides in length or from 15-25 nucleotides in length, and may be DNA, RNA or synthetic nucleic acid, and may be chemically or biochemically modified or may contain non-natural or derivatized nucleotide bases, as will be appreciated by those skilled in the art. Also included are synthetic molecules that mimic polynucleotides in their ability to bind to a designated sequence to form a stable hybrid. Such molecules are known in the art and include, for example, peptide nucleic acids (PNAs) in which peptide linkages substitute for phosphate linkages in the backbone of the molecule.

By "polynucelotide" is meant the polymeric form of deoxyribonucleotides (adenine, guanine, thymine, or cytosine) in either its single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

By "primer" is meant an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 10 or more nucleotides, preferably 15-100 nucleotides and more preferably 15-25 nucleotides, although it may contain fewer nucleotides or more nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A labeled oligonucleotide or primer may be utilized in the methods, assays and kits of the present invention. The labeled oligonucleotide may be utilized as a primer in PCR or other method of amplification and may be utilized in analysis, as a reactor or binding partner of the resulting amplified product. In certain methods, where sufficient concentration or sequestration of the subject nucleic acid has occurred, and wherein the oligonucleotide label and methods utilized are appropriately and sufficiently sensitive, the nucleic acid may be directly analyzed, with the presence of, or presence of a particular label indicative of the result and diagnostic of the presence or absence of a particular single nucleotide polymorphism (SNP). After the labeled oligonucleotide or primer has had an opportunity to react with sites within the sample, the resulting product may be examined by known techniques, which may vary with the nature of the label attached. The label utilized may be radioactive or non-radioactive, including fluorescent, colorimetric or enzymatic. In addition, the label may be, for instance, a physical or antigenic tag which is characterized by its activity or binding.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Description:

The present invention extends to diagnostic assays, kits and methods for determining the gamma glutamyl hydrolase (GGH) genotype of a subject with respect to the single nucleotide polymorphism (SNP) identified at a position in exon 5 of the human GGH gene corresponding to nucleotide 511 of Genbank sequence accession no. NM 003878 (position 511 of SEQ ID No. 1; also referred to herein in Example 1 as 452C>T and T127I), thereby providing a means to determine the expression or activity of GGH in the subject. This is particularly relevant in determining and assessing interpatient variation in the metabolism of drugs which involves GGH activity.

In the wildtype GGH gene the nucleotide at the position corresponding to nucleotide 511 of Genbank sequence accession no. NM 003878 (position 511 of SEQ ID No. 1) is a cytosine and is part of the three nucleotide codon ACT which encodes a threonine (THR) in the GGH protein. The mutation identified herein associated with lower levels of GGH activity is a change in the nucleotide at this position to a thymine, which changes the corresponding codon to ATT which encodes an isoleucine (ILE) in the mutant GGH protein.

Subjects who have a cytosine on each GGH allele at the position corresponding to position 511 of SEQ ID No.1 are expected to have high levels of GGH activity relative to subjects who have a thymine on each GGH allele at this position. Subjects who have a cytosine on one GGH allele at this position and a thymine on the other GGH allele at this position are expected to have an intermediate level of GGH activity lower than subjects who have a cytosine on each GGH allele at this position and higher than subjects who have a thymine on each GGH allele at this position. Therefore one can predict the relative level of GGH activity in a subject by determining the identity of the nucleotide corresponding to position 511 of SEQ ID No. 1 in each GGH allele of the genome of the subject.

The nucleotide at this position in the GGH gene can be identified from a sample of nucleic acid obtained from a subject (DNA or RNA) by any desired conventional means applicable to this polymorphism. This includes determining the identity of this nucleotide using standard sequencing techniques, restriction fragment length polymorphism (RFLP) analysis, PCR-RFLP analysis, bioelectronic microchip analysis (see U.S. Pat. No. 6,468,742 granted Oct. 22, 2002), degradation of a fluorescent or tagged sequence (see U.S. Pat. No. 6,682,887 granted Jan. 27, 2004 and U.S. Pat. No. 6,322,980 granted Nov. 27, 2001), mass spectrometry (see U.S. Pat. No. 6,613,509 granted Sep. 2, 2003), single-strand conformational polymorphism analysis, single base extension, Taq Man real-time PCR genotyping, heteroduplex analysis, allele specific amplification, single molecule dilution, coupled amplification and sequencing, or any other standard hybridization technique using oligonucleotide primers designed to differentially hybridise to the GGH gene or a fragment thereof depending upon the identity of the nucleotide at this position. Preferably, the method of identification used will allow identification of this nucleotide on each allele of the GGH gene in the nucleic acid sample. However, methods which allow detection of the presence or absence of the mutant nucleotide (thymine) at this position on either of the GGH alleles present in a nucleic acid sample are useful.

An Ase1 restriction site (ATTAAT) is created by the presence of a thymine at the position on the GGH gene corresponding to position 511 of SEQ ID No.1. RFLP analysis can be used to detect the presence or absence of this Ase1 restriction site at this location on the GGH gene. The presence of an Ase1 restriction site at this location indicates that the GGH gene has a thymine at the position corresponding to position 511 of SEQ ID No.1. The absence of an Ase1 restriction site at this location indicates that the GGH gene has a cytosine at the position corresponding to position 511 of SEQ ID No. 1.

To facilitate detection, the portion of the GGH gene containing this SNP can be amplified from a nucleic acid sample using standard polymerase chain reaction (PCR) techniques. See Bruce Alberts, Alexander Johnson, Julian Lewis, Martin Raff, Keith Roberts, Peter Walter (eds), Molecular Biology of THE CELL (4th edition), pub. by Garland Science, NY pp. 508-509 (2002). Application of these techniques involves the use of oligonuclotide primers which hybridise to portions of the GGH gene on either side of the SNP. These oligonucltide primers represent another aspect of the present invention.

In addition to the primary SNP associated with low GGH activity, the inventors also identified two additional SNPs within the GGH gene associated with low GGH activity. These SNPs can be detected using the same methods described above for the primary SNP. The present invention extends to diagnostic assays, kits and methods for determining the gamma glutamyl hydrolase (GGH) genotype of a subject with respect to these two additional SNPs.

One of these SNPs occurs in exon 2 of the human GGH gene at a position corresponding to nucleotide 233 of Genbank sequence accession no. NM 003878 (position 233 of SEQ ID No. 1; also referred to herein in Example 1 as 174G>A and A34A). In the wildtype GGH gene the nucleotide at this position is a guanine. The mutation identified herein associated with lower levels of GGH activity is a change in the nucleotide at this position to an adenine, which is a silent mutation that does not change the amino acid encoded by the corresponding codon.

The other SNP identified by the inventors as associated with low GGH activity occurs in the 3' untranslated region of the GGH gene at a position corresponding to nucleotide 1161 of Genbank sequence accession no. NM 003878 (position 1161 of SEQ ID No. 1; also referred to herein in Example 1 as 1102A>G). In the wildtype GGH gene the nucleotide at this position is an adenine. The mutation identified herein associated with lower levels of GGH activity is a change in the nucleotide at this position to a guanine.

Kits useful for determining the genotype of the GGH gene at the polymorphic locations taught herein as associated with low GGH activity are also provided. Such kits may contain oligonucleotide primers that can be used to determine the identity of the nucleotide at the polymorphic location of interest. For example, a kit designed for determining the identity of the nucleotide at the position corresponding to nucleotide 511 of SEQ ID No. 1 could contain an oligonuceotide primer having the sequence set forth in SEQ ID No. 7 or SEQ ID No. 8. Such kits may also contain forward and reverse oligonucleotide primers designed to amplify the portion of the GGH gene containing the polymorphism(s) of interest. For example a kit designed for determining the genotype of the GGH gene at the polymorphic location corresponding to nucleotide 511 of SEQ ID No. 1 could contain a forward oligonucleotide primer having the sequence set forth in SEQ ID No. 3 and a reverse forward oligonucleotide primer having the sequence set forth in SEQ ID No. 4, or a forward oligonucleotide primer having the sequence set forth in SEQ ID No. 5 and a reverse forward oligonucleotide primer having the sequence set forth in SEQ ID No. 6. Such kits may also include other standard components useful in the amplification process, such as appropriate buffer solutions and polymerases used to catalyze the DNA amplification process. Such kits may also include standard components for sequencing the amplified portion of the GGH gene or for determining the identity of the nucleotide at the polymorphic position on the amplified portion of the GGH gene.

The present invention may be better understood by reference to the following non-limiting examples. These examples are presented in order to more fully illustrate the invention through the description of particular embodiments. These examples should in no way be construed as limiting the scope of the invention.

EXAMPLES

Example 1

A Substrate Specific Functional Polymorphism of Human γ-Glutamyl Hydrolase Alters Catalytic Activity and Methotrexate Polyglutamate Accumulation in Acute Lymphoblastic Leukemia Cells Summary A significant inverse relationship was found between γ-glutamyl hydrolase (GGH) activity and the accumulation of long-chain methotrexate polyglutamates (MTX-PG$_{4-7}$) in non-hyperdiploid B-lineage ALL leukemia cells after uniform treatment with high-dose methotrexate (HDMTX) (1 g/m$^2$ IV). To identify genetic polymorphisms that alter the function of human GGH the GGH exons from children with acute lymphoblastic leukemia (ALL), who had a 7.8-fold range of GGH activity in their ALL cells at diagnosis, were sequenced. SNP 452C>T (T127I; a change from a cytosine to a thymine at a position corresponding to nucleotide 511 of Genbank sequence accession no. NM 003878) was found among patients with low GGH activity, but not found in patients with high GGH activity. Computational modeling indicated that the T127I substitution alters the molecular surface conformation at the catalytic cleft-tail on GGH, which is predicted to alter binding affinity with long chain methotrexate polyglutamates. Enzyme kinetic analysis of heterologously expressed GGH revealed a significantly higher K$_m$ (2.7-fold) and lower catalytic efficiency (V$_{max}$/K$_m$ reduced 67%) of the T127I variant compared to wild-type GGH using MTX-PG$_5$ as substrate. SNP 452C>T was also associated with lower GGH activity in hyperdiploid B-lineage and T lineage ALL leukemia cells. Caucasians (10.0%; 95% CI: 6.7-13.3%; n=155) were found to have significantly higher frequency of the Ile127 allele than African-Americans (4.4%; 95% CI: 1.2-7.5%; n=80) (p=0.033). These studies have demonstrated a substrate specific functional SNP (452C>T) in the human GGH gene, that is associated with lower catalytic activity and higher accumulation of long-chain MTX-PG in leukemia cells of patients treated with HDMTX.

Introduction

Methotrexate (MTX) is an antifolate that is used essentially in all treatment protocols for childhood acute lymphoblastic leukemia (ALL) (Chabner, B. A. et al., "Polyglutamation of methotrexate. Is methotrexate a prodrug?" *J Clin Invest* 76:907-912 (1985); Gorlick, R. et al., "Intrinsic and acquired resistance to methotrexate in acute leukemia". *N Engl J Med* 335:1041-1048 (1996); Bertino, J. R., Karnofsky memorial lecture. Ode to methotrexate. *J Clin Oncol* 11:5-14 (1993); Camitta, B. et al., "Intensive intravenous methotrexate and mercaptopurine treatment of higher-risk non-T, non-B acute lymphocytic leukemia: A Pediatric Oncology Group study" *J Clin Oncol* 12:1383-1389 (1994); Schorin M. A., et al., "Treatment of childhood acute lymphoblastic leukemia: results of Dana-Farber Cancer Institute/Children's Hospital Acute Lymphoblastic Leukemia Consortium Protocol 85-01" *J Clin Oncol* 12:740-747 (1994); Niemeyer, C. M. et al., "Low-dose versus high-dose methotrexate during remission induction in childhood acute lymphoblastic leukemia (Protocol 81-01 update)" *Blood* 78:2514-2519 (1991); Mahoney, D. H., Jr., et al., "Intermediate-dose intravenous methotrexate with intravenous mercaptopurine is superior to repetitive low-dose oral methotrexate with intravenous mercaptopurine for children with lower-risk B-lineage acute lymphoblastic leukemia: a Pediatric Oncology Group phase III trial". *J Clin Oncol* 16: 246-254 (1998); Evans, W. E. et al., "Conventional compared with individualized chemotherapy for childhood acute lymphoblastic leukemia" *N Engl J Med* 338:499-505 (1998); Pui, C. H. et al., "Acute lymphoblastic leukemia" *N Engl J Med* 339: 605-615 (1998)).

After its entry into cells, MTX is rapidly converted to γ-glutamyl polyglutamates through the action of folypolyglutamate synthetase (FPGS, EC 6.3.2.17), which sequentially adds up to 6 glutamyl residues to MTX (Goldman, I.D. et al., "Carrier-mediated transport of the folic acid analogue, methotrexate, in the L1210 leukemia cell" *J Biol Chem* 243: 5007-5017 (1968); Zhao, R. et al., "Resistance to antifolates" *Oncogene* 22:7431-7457 (2003); Shane, B., "Folylpolyglutamate synthesis and role in the regulation of one-carbon metabolism", *Vitam Horm* 45:263-335 (1989)).

Long chain polyglutamates (MTXPG$_{4-7}$) are more avid inhibitors of folate-dependent enzymes and are also retained longer within cells, thereby increasing MTX's prolonging their antifolate effects (Chabner, B. A. et al., id; Masson, E. et al., "Accumulation of methotrexate polyglutamates in lymphoblasts is a determinant of antileukemic effects in vivo. A rationale for high-dose methotrexate" *J Clin Invest* 97:73-80 (1996)). Higher accumulation of MTXPG has been associated with increased cytotoxicity and treatment response in childhood ALL (Masson, E. et al., id; Whitehead, V. M. et al., "Accumulation of methotrexate and methotrexate polyglutamates in lymphoblasts at diagnosis of childhood acute lymphoblastic leukemia: a pilot prognostic factor analysis" *Blood* 76:44-49 (1990)).

Significant lineage and ploidy differences have been observed in MTX-PG accumulation in ALL cells, with T-lineage ALL having the lowest MTX-PG accumulation and hyperdiploid (>50 chromosomes) B-lineage ALL having the highest MTX-PG accumulation (Synold, T. W. et al., "Blast cell methotrexate-polyglutamate accumulation in vivo differs by lineage, ploidy, and methotrexate dose in acute lymphoblastic leukemia" *J Clin Invest* 94:1996-2001 (1994); Whitehead, V. M. et al., "Accumulation of high levels of methotrexate polyglutamates in lymphoblasts from children with hyperdiploid (greater than 50 chromosomes) B-lineage acute lymphoblastic leukemia: a Pediatric Oncology Group study" *Blood* 80:1316-1323 (1992)). The underlying mechanisms for these differences include lower FPGS activity in T-ALL (Barredo, J. C. et al., "Differences in constitutive and post-methotrexate folylpolyglutamate synthetase activity in B-lineage and T-lineage leukemia" *Blood* 84:564-569 (1994)) and higher reduced folate carrier (RFC) expression in hyperdiploid B-lineage ALL (Belkov, V. M. et al., "Reduced folate carrier expression in acute lymphoblastic leukemia: a mechanism for ploidy but not lineage differences in methotrexate accumulation" *Blood* 93:1643-1650 (1999)). However, following uniform treatment with HDMTX, there remain substantial inter-individual differences in MTX-PG accumulation within each of the three lineage and ploidy subtypes of ALL, for reasons that have not been fully elucidated.

γ-Glutamyl hydrolase (GGH, also known as folypolyglutamate hydrolase, FPGH, EC 3.4.19.9) is a lysosomal peptidase that catalyzes the removal of γ-linked polyglutamates, converting long-chain MTX-PG into shorter-chain MTX-PG and ultimately to MTX. This allows MTX to be effluxed from cells and thereby reduces the overall effectiveness of MTX (Galivan, J. et al., "Glutamyl hydrolase: properties and pharmacologic impact" *Semin Oncol* 26:33-37 (1999); Rhee, M. S. et al., "Characterization of human cellular gamma-glutamyl hydrolase" *Mol Pharmacol* 53:1040-1046 (1998); Panetta, J. C. et al., "Methotrexate intracellular disposition in acute lymphoblastic leukemia: a mathematical model of gamma-glutamyl hydrolase activity" *Clin Cancer Res* 8:2423-2429 (2002)). The human GGH gene spans 24 kb on chromosome 8 (q12.23-13.1) and comprises nine exons (Yin, D. et al., "Structural organization of the human gamma-glutamyl hydrolase gene" *Gene* 238: 463-470 (1999)). The crystal structure of human GGH has been determined and a model for substrate recognition and hydrolysis has been proposed (Li, H. et al., "Three-dimensional structure of human gamma-glutamyl hydrolase. A class I glatamine amidotransferase adapted for a complex substate" *J Biol Chem* 277: 24522-24529 (2002); Chave, K. J, et al., "Molecular modeling and site-directed mutagenesis define the catalytic motif in human gamma-glutamyl hydrolase" *J Biol Chem* 275:40365-40370 (2000)). Cellular GGH is predominantly lysosomal, with an acidic pH optimum, functioning as either an endopeptidase or exopeptidase, exhibiting species differences in these functions (Elsenhans, B. et al., "Isolation and characterization of pteroylpolyglutamate hydrolase from rat intestinal mucosa" *J Biol Chem* 259:6364-6368 (1984); Samuels, L. L. et al., "Hydrolytic cleavage of methotrexate gamma-polyglutamates by folylpolyglutamyl hydrolase derived from various tumors and normal tissues of the mouse" *Cancer Res* 46:2230-2235 (1986); Bhandari, S. D. et al., "Properties of pteroylpolyglutarnate hydrolase in pancreatic juice of the pig" *J Nutr* 120:467-475 (1990); Yao, R. et al., "Human gamma-glutamyl hydrolase: cloning and characterization of the enzyme expressed in vitro" *Proc Natl Acad Sci USA* 93:10134-10138 (1996)). Human GGH has a higher affinity for the longer chain MTX polyglutamates, cleaving multiple glutamyl residues, with highest activity at the outermost or two outermost residues in the polyglutamate chain (Panetta, J. C., et al., id).

The current study reveals marked heterogeneity of GGH activity in human ALL cells and documents a significant inverse relation between GGH activity and MTX-PG$_{4-7}$ in non-hyperdiploid B-lineage ALL. Further, we identified several germ-line polymorphisms in the human GGH gene, one of which (452C>T, T127I) significantly alters GGH catalytic activity, and is associated with low GGH activity and high MTXPG accumulation in ALL blasts of patients treated with high-dose MTX. This establishes a previously unrecognized inherited determinant of MTX disposition in human leukemia cells, providing new insights toward optimizing treatment with this widely used antileukemic agent.

Methods

Patients, treatment and isolation of leukemia cells: Leukemia cells were isolated by bone marrow aspirates from children with newly diagnosed ALL who were treated on St Jude Children's Research Hospital Total XV protocol (Pui, C. H. et al., "Rational and design of total therapy study XV for newly diagnosed acute lyphoblastic leukemia" *Annals of Hematology* 2003), after approval by our institutional review board and appropriate informed consent. All patients received initial therapy with high-dose intravenous MTX (1 g/m$^2$), with supportive care as previously reported (Cheok, M. H. et al., "Treatment-specific changes in gene expression discriminate in vivo drug response in human leukemia cells" *Nat Genet* 2003; 34: 85-90). Bone marrow aspirates were obtained at diagnosis and 42 h after the start of MTX therapy. The diagnosis of ALL, including immunophenotyping, and cytogenetic analyses, were performed as previously described (Pui, C. H. et al. 1998, id; Yeoh, E. J. et al., "Classification, subtype discovery, and prediction of outcome in pediatric acute lymphoblastic leukemia by gene expression profiling" *Cancer Cell* 1:133-143 (2002)). Leukemic blast cells were isolated by Ficoll-Hypaque gradient as previously described (Synold, T. W. et al., id)).

Analysis of human GGH activity and MTXPG accumulation in ALL cells: $5-10 \times 10^6$ lymphoblast cells isolated from diagnostic bone marrows were resuspended in sucrose solution (0.25 M sucrose, 1 mM EDTA, 10 mM Hepes-NaOH, pH 7.4). Total cell lysate was obtained by treating with 0.1% triton x-100. Human GGH activity was determined using MTEN buffer with 2 mM DTT and the reaction products were analyzed by HPLC, as previously described (Panetta, J. C. et al., id). GGH activity was calculated as the total amount of product formed per hour per μg protein.

MTX-PGs were measured in bone marrow ALL blasts obtained 42 h from the start of MTX. MTX and its polyglutamated metabolites were separated by HPLC and quantitated by radioenzymatic assay (Synold, T. W. et al., id). The limit of detection of this assay was 0.02 pmol/$10^6$ cells. All results are expressed as picomoles MTXPG per $10^9$ cells.

Identification of genetic polymorphisms and GGH genotyping: Genomic DNA was extracted from normal blood cells with TriReagent (MRC, OH). Using Vector NTI Advance (InforMax. MD), primers were designed for PCR amplification of human GGH exons including intron/exon boundaries in genomic DNA. PCR amplification was performed according to the manufacturer's protocol, using Expand High Fidelity PCR system or GC-RICH PCR System (Roche, IN). Sequence analysis was performed on an ABI Prism 3700 Automated Sequencer using the PCR primers. The nucleotide sequences were assembled using the Phred-Phrap Consed package (http://droog.mbt.washington.edu/PolyPhred.html University of Washington, Seattle) for the detection of heterozygous single nucleotide polymorphisms. GenBank accession numbers: GGH genomic DNA, NT_008183.17; GGH promoter region, AF147081.

Genotyping for the single nucleotide polymorphism (SNP) 452C>T in exon 5 was carried out by direct sequencing using the following two sets of primers:

Region: Exon 4 and Exon 5

```
Forward Primer (5'-3'):
TGTTTTCTGTGTGTGTATGGGTCGG      (SEQ ID No. 3)

Reverse Primer (5'-3'):
TGCTACTTACTAATCCTGCCCAGCA      (SEQ ID No. 4)
```

Region: Exon 5

```
Forward Primer (5'-3'):
TGTTTTCCAGCCTGTGTGGGAG         (SEQ ID No. 5)

Reverse Primer (5'-3'):
GGATGGTCATTCACATCTTCAACC       (SEQ ID No. 6)
```

Allele and genotype frequency were calculated based on the observed number of the two different alleles, Thr127 and Ile127, which were derived from genotype data in each ethnic group. Exact chi square test and Fisher's exact test were used to compare the observed and expected allele and genotype frequencies among different populations. Statistical analyses were performed using software R (http://www.r-project.org).

Structural modeling and docking: Structural modeling of the variant GGH containing T127I amino acid change was built on Swiss-Model server for automatic model building (http://www.expasy.org/swissmod/SWISS-MODEL.html). The model was built based on sequence alignment using wild type GGH (PDB code: 1L9X) as the template. The reported model was visualized using SYBYL program. Computational docking was performed using the flexible docking method FlexX (Rarey, M. et al., "A fast flexible docking method using an incremental construction algorithm" *J Mol Biol* 261:470-489 (1996)). Cscore uses five different scoring functions to quantify the affinity of a small molecule ligand to the protein active site. A model with the highest Cscore was selected to represent the intermediate complex for the cleavage of the gamma-glutamyl link. Residues Gly74-Arg79, Cys110-Leu 118, Ala168-Trp173, His220 and Glu222 were defined as active sites of GGH with a sphere of 6.5 Å around each residue to generate docking model. The MTX-PG$_5$ and MTX-PG$_2$ substrates were prepared in the SYBYL mol2 format, with all hydrogens added and formal charges assigned after energy minimization. It has been proposed that the substrate binding and catalytic mechanism of human GGH is similar to the GATase domains of carbamoyl-phosphate synthetase (eCPS) (Li, H. et al., id). To examine the accuracy of the interaction model of MTX-PG$_5$ with GGH, the crystal structure of carbamoyl-phosphate synthetase (eCPS) variant H353N-glutamine thioester complex (PDB code: 1A9X) was superimposed onto the GGH containing MTX-PG$_5$ substrate by least-squares fitting of α-carbons of 20 residues around the active site.

The binding free energy is calculated by using SYBYL minimize function. All energy minimization was carried out using Tripos force-field (Clark, M. et al., "Validation of the General-Purpose Tripos 5.2 Force-Field" *Journal of Computational Chemistry* 10:982-1012 (1989)) with a distance dependent dielectric constant "D=80.0" and Gasteiger-Huckel charge (http://www.tripos.com). The binding free energy per molecule was computed using the formula:

$$\Delta\Delta G = \Delta G_{complex} - \Delta G_{protein} - \Delta G_{ligand}$$

All minimization energies were obtained after 1000 maximum iterations with a termination gradient of 0.005 kcals/mol.

Wild-type human GGH cloning and site-directed mutagenesis: A cDNA encoding the 294 amino acids of human GGH (with out leading peptide) was cloned by RT-PCR and TA cloning (Invitrogen, Carlsbad, Calif.) using RNA isolated from human CEM cells. Plasmid DNA was purified using the mini prep kit (Qiagen, Santa Clarita, Calif.). After sequencing, the selected cDNA clone was subcloned into the pET28b vector (Novagen, Madison, Wis.) from Nde1 and BamH1 sites, and an N-terminal HisTag was added. This HisTag enabled the purification of large quantities of protein and had no effect on GGH activity (Chave, K. J. et al., 2000, id). Site-directed mutagenesis was performed with the Quick-Change II kit (Stratagene, La Jolla, Calif.) according to the manufacturer's protocol. The primers used for mutagenesis of wild-type human GGH to T127I were

```
                              (forward; SEQ ID No. 7)
5'-GTGGAGAGTGCTTATTAATTGCCACAGATACTGTTGAC-3';
and
                              (reverse; SEQ ID No. 8)
5'-GTCAACAGTATCTGTGGCAATTAATAAGCACTCTCCAC-3'.
```

Both wild-type and recombinant variant form of human GGH clones were further confirmed by sequencing.

Expression and characterization of T127I variant GGH: Plasmids carrying wild-type and T127I variant GGH were used to transform E. coli strain BL21(DE3)pLysS competent cells (Novagen, Madison, Wis.). The E. coli cells were grown in LB medium containing 30 μg/ml kanamycin and 34 μg/ml chloramphenicol at 37° C. to $OD_{600}$ about 0.6 and expression was induced with 1 mM isopropyl-β-D-thiogalactoside for 3 h. Cells were harvested by centrifugation at 5,000 g for 5 min at 4° C., and were kept as a frozen pellet at −70° C. Target proteins were extracted using BugBuster His-Bind Purification kit (Novagen, Madison, Wis.), followed by gel filtration chromatography at 4° C. on a HiLoad 26/60 S200 Superdex column (Amersham Pharmacia Biotech, Sweden) in 0.05 M sodium acetate buffer, pH5.5, containing 0.05 M 2-mercaptoethanol, 1 M NaCl, and 1 mM EDTA. Fractions containing target proteins were pooled and proteins were concentrated using Viva Cell 70 ml Concentrator, followed by Viva Cpin 2 ml Concentrator (Vivascience, Edgewood, NY).

Wild-type and T127I variant forms of human GGH were separated using NuPAGE™ 4-12% Bis-Tris Gel (Invitrogen, Carlsbad, Calif.). Protein bands were visualized by silver staining (Amersham Pharmacia Biotech, Sweden). Western blot was carried out as described (Tai, H. L. et al., "Thiopurine S-methyltransferase deficiency: two nucleotide transitions define the most prevalent mutant allele associated with loss of catalytic activity in Caucasians" *Am J Hum Genet* 58:694-702 (1996)). Polyclonal anti-human GGH rabbit antibody was kindly provided by Drs Thomas J. Ryan and John. GGH activity was measured using MTEN buffer with 25 mM DTT. The assay mixture without substrate was incubated at 37° C. for 20 min, followed by incubation with substrate at 37° C. for 5 min and boiling for 5 min. In each experiment, wild-type and variant GGH were analyzed in parallel using varying concentrations of $MTX-PG_5$ or $MTX-PG_2$ as substrate. The substrate and the reaction products were analyzed by HPLC, and GGH activity was calculated by total amount of product formed per min per μg protein. Two independent experiments were carried on with each substrate. Nonlinear least-squares regression was used to estimate $K_m$ and $V_{max}$ by fitting a Michaels-Menten model as described earlier (Panetta, J. C. et al., id).

Results

GGH activity in lineage and ploidy subtypes of ALL: GGH activity was significantly different among ALL subtypes (Kruskal-Wallis test, p=0.025), with T lineage ALL cells having significantly higher GGH activity compared to B lineage ALL (Mann-Whitney U test, p=0.011). There was also substantial heterogeneity in GGH activity in ALL cells within each of these ALL subtypes. The largest range of GGH activity was found among patients with non-hyperdiploid B-lineage ALL (7.8 fold), compared to patients with T lineage ALL (3.7 fold) and hyperdiploid B-lineage ALL (3.0 fold).

MTX-PG accumulation and GGH activity among non-hyperdiploid B-lineage ALL patients: There was a 14.6 fold range of long chain MTX-PG ($MTX-PG_{4-7}$) accumulation following uniform treatment with HDMTX, among patients with non-hyperdiploid B-lineage ALL. When these patients were sub-divided according to their ALL GGH activity (i.e., low, intermediate and high GGH activity defined as the top 25%, intermediate 50%, and bottom 25%), accumulation of long-chain $MTX-PG_{4-7}$ in ALL blasts was inversely related to GGH activity. Similarly, there was an 18.5 fold range of total MTX-PG ($MTX-PG_{2-7}$) accumulation, which was inversely related to GGH activity in ALL cells. In contrast, there was not a significant relation between GGH activity and short chain MTX-PG ($MTX-PG_{2-3}$) accumulation.

Polymorphisms in human GGH: By sequencing GGH exons and intron/exon boundaries in genomic DNA from five patients with high GGH activity and four with low GGH activity, five SNPs were identified, at bases 16T>C, 91G>A, 174G>A, 452C>T and 1102A>G, relative to the A of the translation start codon. 16T>C, 452C>T and 1102A>G are recently reported by another group (Chave, K. J. et al., "Identification of single nucleotide polymorphisms in the human gamma-glutamyl hydrolase gene and characterization of promoter polymorphisms". *Gene* 319: 167-175 (2003)).

The SNP (452C>T) producing a non-conservative amino acid substitution of threonine (Thr A<u>C</u>T) to isoleucine (Ile A<u>T</u>T) at position 127 in exon 5 of human GGH, was only detected in patients with low GGH activity (2 of 4), but in none of the 5 patients with high GGH activity. A novel synonymous SNP in exon 2 (174G>A, A34A) and a SNP located in the 3'UTR (1102A>G, exon 9) were also found only in patients with low GGH activity (1 of 4, and 2 of 4, respectively). A novel non-synonymous SNP (91G>A, A7T) located in exon 1 was found in 2 of 4 patients with low GGH activity and 1 of 5 with high GGH activity. The non-synonymous SNP (16T>C) (dbSNP Ref# rs1800909) in the endoplasmic reticulum targeting sequence of human GGH was found in 3 patients with low GGH activity and 4 patients with high GGH activity.

Structural model of the T127I variant GGH and its interaction with MTX-PG: Using crystal structure wild-type GGH, we established a computational model of the T127I variant GGH. The model estimated that the T127I substitution changes the side chain orientation of residues Cys124 and Leu125, resulting in an alteration of molecular surface around the mutated residue, from a flat to a protruded conformation.

In order to estimate how these conformational changes alter substrate binding, the FlexX program was used to build a binding model of $MTX-PG_5$ onto wild-type GGH. The model indicated that the third glutamate in $MTX-PG_5$ can overlap onto the glutamine thioester intermediate, within 4 Å from Cys110, which is an acceptable range for the Cys110 nucleophilic attacking cleavage site between the third and fourth glutamate. To fit the GGH substrate binding cleft well without steric conflicts, the p-aminobenzoyl group of $MTX-PG_5$ was stacked in the patch of hydrophobic residues including Cys124, Leu125, Leu126 and Trp173, while the pterin group was flexibly placed outside of the cleft. The accuracy of this interaction model was examined by superimposing a crystal structure of eCPS variant H353N-glutamine thioester complex onto the GGH containing $MTX-PG_5$ substrate. In T127I variant GGH, side chain shift at Cys124 and Leu125 narrowed the gap between Leu125 and Trp173 from 11.3 Å in wild-type to 7 Å in T127I variant, reducing the space for accommodating the p-aminobenzoyl group of $MTXPG_5$. The binding free energy of $MTX-PG_5$ was increased from −48.7 kcals/mol with wild-type GGH to −30.8 kcals/mol with T127I variant. Thus, the structural modeling indicates that the T127I mutation may reduce GGH catalytic activity for long chain MTX-PG by affecting substrate binding affinity.

We also constructed a binding model of $MTX-PG_2$ onto wild-type and T127I variant GGH. With only two glutamate residues, the pteroyl group of $MTX-PG_2$ was placed into the tail pocket, surrounded by residues of Asp77, Leu78, Arg79, Leu111, Leu126 and Trp173. This estimated that local conformational changes at loop 124-127 in the T127I variant have a very modest affect on the interaction between $MTX-PG_2$ and GGH. The estimated binding free energy of $MTX-PG_2$ with wild-type and T127I GGH were −29.4 kcals/mol, and −30.5 kcals/mol respectively.

Expression and functional characterization of T127I variant protein: We cloned the wild-type human GGH and constructed T127I variant protein by site directed mutagenesis. The two expressed proteins were separated by SDS-PAGE gel electrophoresis, and detected in equal quantities by silver staining and Western blot.

Both wild-type and T127I variant human GGH protein exhibited Michaelis-Menten kinetics with MTXPG ($PG_2$ or $PG_5$) as substrate. T127I variant significantly increased $K_m$ for $MTXPG_5$ (2.7 fold, p=0.021), but there was not a significant difference in $V_{max}$ between the wild-type and T127I variant. The catalytic efficiency ($V_{max}/K_m$) of T127I variant for $MTXPG_5$ was significantly reduced (by 67.5%, p=0.003). Consistent with our structural modeling, enzyme kinetic analysis indicated that the T127I variant significantly reduced GGH binding affinity for long chain MTX-PG ($MTX-PG_5$), but had less effect on short-chain $MTX-PG_2$, for which there was not a significant difference in $K_m$, $V_{max}$ or catalytic efficiency.

Concordance of phenotype and genotype for SNP 452C>T (T127I): The 452C>T genotype was determined in 66 patients with ALL (38 non-hyperdiploid B-lineage; 12 hyperdiploid B-lineage; 16 T lineage), in whom leukemia cell GGH activity was measured in ALL cells. Within each ALL subtype, when patients were grouped as low, intermediate and high GGH activity, the 452C>T SNP (T127I) was not found in any patients with high GGH activity (FIG. 1). In contrast, the allele frequency of this SNP was higher among patients with low GGH activity, in non-hyperdiploid B-lineage, hyperdiploid B-lineage or T lineage ALL (20.0%, 16.7% and 12.5% respectively, FIG. 1). The 452C>T SNP was also found in patients with intermediate GGH activity, but at a frequency intermediate to the low and high GGH activity patients (11.1%, 8.3% and 6.3% respectively; FIG. 1). For the entire group of patients studied (n=66), the frequency of the 452C>T SNP was significantly different among patients with low (17.6%), intermediate (9.4%) and high (0%) GGH activity respectively (Exact chi square test, p=0.025).

The allele and genotype frequencies of the human GGH Thr127Ile polymorphism among 235 children with ALL (155 Caucasians and 80 African-Americans) revealed significant ethnic differences. Caucasians had a significantly higher frequency of the Ile127 allele (10.0%, 95% CI: 6.7%-13.3%) than in African-American (4.4%, 95% CI: 1.2-7.5%) (Fisher's exact test, p=0.033). The allele and genotype frequencies for these two ethnic groups were in Hardy-Weinberg equilibrium (all p=1).

Discussion

In the present study, a non-synonymous SNP 452C>T (T127I) was identified in the human GGH gene that significantly alters catalytic activity for cleavage of long-chain MTXPG and is associated with altered in vivo GGH activity and long-chain MTXPG accumulation in ALL cells. We documented a 7.8-fold range of GGH activity in ALL cells obtained at diagnosis from children with non-hyperdiploid B-lineage ALL, a 14.6 fold range of long-chain methotrexate polyglutamate ($MTX-PG_{4-7}$) accumulation, and a significant inverse relation between GGH activity and $MTX-PG_{4-7}$ accumulation in ALL cells after uniform HDMTX treatment (1 g/m² IV). We also documented substantial heterogeneity in GGH activity in other subtypes of ALL (i.e., 3.0 fold range in hyperdiploid B-lineage and 3.7 fold range in T lineage ALL), but the number of available patients precluded assessment of the relation between GGH activity and MTXPG accumulation in these more rare subtypes of ALL.

Because cellular accumulation of long-chain MTXPG is advantageous in ALL therapy, and human GGH has a different affinity for longer-chain and short-chain MTX polyglutamates (Panetta, J. C. et al., id), we used $MTX-PG_5$ as the substrate for measuring GGH activity in ALL cells. The 452C>T SNP was found in a higher frequency among patients with low GGH activity, and was not found in patients with high GGH activity. For the entire group of patients studied, the frequency of the 452C>T SNP was significantly different among patients with low (17.6%), intermediate (9.4%) and high (0%) GGH activity, respectively (Fisher chi square test, p=0.025). Among patients with non-hyperdiploid B-lineage, hyperdiploid B-lineage and T lineage childhood ALL, the allele frequency of the 452C>T (T127I) SNP was 20.0%, 16.7% and 12.5% in patients with low GGH activity, and 11.1%, 8.3% and 6.3% in patients with intermediate GGH activity, and not detected in any patient with high GGH activity (FIG. 1). Recently, the 452C>T SNP was also identified in human GGH from breast cancer tissue and leukemia cell lines (Chave, K. J. et al., "Identification of single nucleotide polymorphisms in the human gamma-glutamyl hydrolase gene and characterization of promoter polymorphisms". *Gene* 319:167-175 (2003)). Using short chain MTXPG ($MTXPG_2$) as the substrate for measuring GGH activity, Chave et al. reported that T127I mutation did not change GGH activity (Chave, K. J. et al., 2003, id). Our findings by both biochemical analysis and structure modeling reveal a significant influence of the 452C>T SNP on GGH hydrolysis of the more pharmacologically important long-chain polyglutamate substrate.

Human GGH contains an L-shaped catalytic cleft on the surface, which comprises loops 74-79, 124-127 and strand β9 168-173 with one end closed (cleft-head) and the other end open (cleft-tail) (Li, H. et al., id). Subtracts interaction model indicated p-aminobenzoyl group of $MTX-PG_5$ was stacked in the patch of hydrophobic residues around Leu125 and Trp173. The substitution of Thy127 by Ile narrows the open end of the cleft-tail by changing the side chain orientation of Cys124 and Leu125, reducing the gap between Leu125 and Trp173 to 7 Å in the T127I variant. The binding free energy of $MTX-PG_5$ with T127I variant was increased by 36.8%. Enzyme kinetic analysis revealed a significantly higher $K_m$ (2.7-fold) and lower catalytic efficiency ($V_{max}/K_m$ reduced 67.5%) of T127I recombinant GGH when $MTX-PG_5$ was used as a substrate. With only two glutamate residues, the pteroyl group of $MTX-PG_2$ was placed into the tail pocket. The T127I mutation did not significantly change $K_m$ or catalytic efficiency when short chain MTX-PG ($MTX-PG_2$) was used as a substrate. These data establish that the functional consequences of the 452C>T genetic polymorphism in human GGH is substrate specific, having a greater effect on the more active long-chain MTX-PG.

The identification of a single nucleotide polymorphism that alters the function of human GGH and the disposition of methotrexate in leukemia cells in vivo, represents a new genetic polymorphism that alters drug disposition and effects in humans (Evans, W. E. et al., "Pharmacogenomics-drug disposition, drug targets, and side effects" *N Engl J Med* 348: 538-549 (2003); Evans, W. E. et al., "Pharmacogenomics: translating functional genomics into rational therapeutics" *Science* 286:487-491 (1999)). Differences in the pharmacokinetics and pharmacodynamics of ALL chemotherapy contribute to inter-individual differences in drug effects (Brenner, T. et al, "Pharmacogenomics of childhood acute lymphoblastic leukemia" *Curr Opin Mol Ther* 6:567-578 (2002)) which can alter treatment outcome (Pui, C. H. et al., 1998, id) and may also contribute to racial differences in treatment response (Pui, C. H. et al., "Results of therapy for acute lymphoblastic leukemia in black and white children" *JAMA* 290: 2001-2007 (2003); Kadan-Lottick, N. S. et al., "Survival variability by race and ethnicity in childhood acute lymphoblastic leukemia" *JAMA* 290: 2008-2014 (2003)). The frequency of the 452C>T(T127I) SNP was estimated to be 10.0% (95% CI: 6.7-13.3; n=155) among Caucasians, and 4.4% (95% CI: 1.2-7.5%; n=80) among African-Americans in our study. Thus, this GGH SNP is a relatively common genetic polymorphism with functional consequences that may contribute to inter-individual differences in the disposition and effects of MTX, which may extend to a wide spectrum of malignant and non-malignant diseases for which MTX is given. Because GGH catalyzes the hydrolysis of normal folate polyglutamates, in addition to antifolate polyglutamates, it may have functional consequences for folate homeostasis as well. The fact that this SNP significantly lowers but does not abolish GGH activity, likely means that this SNP will have its most pronounced effects on MTX disposition and effects in patients who have inherited non-functional hypomorphic variants of other genes involved in MTX disposition or folate homeostasis.

Indeed, genetic polymorphisms have been found in several genes involved in the pharmacokinetics or pharmacodynamics of MTX, but this is the first functional polymorphism reported for GGH. For example, a SNP (80G>A, H27R) in the human reduced folate carrier (RFC), the major transporter of MTX into cells, has been associated with higher MTX plasma concentrations in children with ALL and with a worse prognosis (Laverdiere, C. et al., "Polymorphism G80A in the reduced folate carrier gene and its relationship to methotrexate plasma levels and outcome of childhood acute lymphoblastic leukemia" *Blood* 100:3832-3834 (2002)). The frequency of the 80G>A SNP was approximately 58% in genomic DNA from individuals with and without leukemia (Laverdierre, C. et al., id). However, in vitro assays did not reveal any functional changes in MTX transport associated with the RFC 80G>A SNP (Whetstine, J. R. et al., "Single nucleotide polymorphisms in the human reduced folate carrier: characterization of a high-frequency G/A variant at position 80 and transport properties of the His(27) and Arg(27) carriers" *Clin Cancer Res* 7:3416-3422 (2001)); so the mechanism of this association is not known. Two SNPs have been identified in the human methylenetetrahydrofolate reductase (MTHFR) gene, and linked to differences in either the toxicity or efficacy of methotrexate in patients with rheumatoid arthritis (Urano, W. et al., "Polymorphisms in the methylenetetrahydrofolate reductase gene were associated with both the efficacy and the toxicity of methotrexate used for the treatment of rheumatoid arthritis, as evidenced by single locus and haplotype analyses" *Pharmacogenetics* 12:183-190 (2002)). SNP 677C>T (A222V) renders the MTHFR enzyme more thermolabile (Frosst, P. et al., "A candidate genetic risk factor for vascular disease: a common mutation in methylenetetrahydrofolate reductase" *Nat Genet* 10:111-113 (1995)), and is associated with lower cellular pools of methyltetrahydrofolate (Bagley, P. J. et al., "A common mutation in the methylenetetrahydrofolate reductase gene is associated with an accumulation of formylated tetrahydrofolates in red blood cells" *Proc Natl Acad Sci USA* 95:13217-13220 (1998)). This SNP has been associated with increased toxicity from low-dose MTX(Urano, W. et al., id; Weisberg, I. et al., "A second genetic polymorphism in methylenetetrahydrofolate reductase (MTHFR) associated with decreased enzyme activity" *Mol Genet Metab* 64:169-172 (1998); Ulrich, C. M. et al., "Pharmacogenetics of methotrexate: toxicity among marrow transplantation patients varies with the methylenetetrahydrofolate reductase C677T polymorphism" *Blood* 98:231-234 (2001)), but has not been associated with increased toxicity when leucovorin (reduced folate) is given after high-dose MTX (Evans, W. E., "Differing effects of methylenetetrahydrofolate reductase single nucleotide polymorphisms on methotrexate efficacy and toxicity in rheumatoid arthritis" *Pharmacogenetics* 12:181-182 (2002)). Another MTHFR SNP (1298 A>C, E429A) leads to reduced enzyme activity (van der Put, N. M. et al., "A second common mutation in the methylenetetrahydrofolate reductase gene: an additional risk factor for neural-tube defects?" *Am J Hum Genet* 62:1044-1051 (1998)), and has been associated with better efficacy in rheumatoid arthritis patients treated with low-dose MTX (Urano, W., et al., id). A tandem-repeat polymorphism in thymidylate synthase (TS) promoter has been linked to interindividual variability in response to MTX, patients homozygous for a triple repeat are reported to have increased expression of TS and a worse reponse to high-dose MTX (Krajinovic, M. et al., "Polymorphism of the thymidylate synthase gene and outcome of acute lymphoblastic leukaemia" *Lancet* 359: 1033-1034 (2002)). A G>C SNP in the second of three tandem-repeats has been shown to abolish the increased expression of TS (Mandola, M. V. et al., "A novel single nucleotide polymorphism within the 5' tandem repeat polymorphism of the thymidylate synthase gene abolishes USF-1 binding and alters transcriptional activity" *Cancer Res* 63: 2898-2904 (2003)). These findings point to the potential of polygenic studies to reveal more robust and predictive pharmacogenetic models of MTX effects.

It is known that MTX-PG accumulation in leukemia cells differs by ALL lineage (B versus T lineage) and ploidy ($\leq 50$ versus >50 chromosomes). T-lineage ALL accumulates lower MTXPG than B-lineage ALL, in part because of lower expression of folylpolyglutamate synthetase in T-ALL (Barredo, J. C. et al., id), whereas hyper-diploid B-lineage ALL exhibits higher MTX-PG accumulation than non-hyper-diploid B-lineage ALL due to higher expression of the reduced folate carrier (Belkov, V. M. et al., id). However, as documented in the current study and others (Synold, T. W. et al., id), there is substantial heterogeneity within each of these ALL subtypes in the accumulation of MTX-PG after uniform HDMTX therapy. Our current findings indicate that some of the unexplained variability in MTX-PG accumulation can be accounted for by differences in GGH-catalyzed degradation of MTX-PG in ALL cells, which is related in part to a common genetic polymorphism that causes low GGH catalytic activity. This previously unrecognized genetic determinant of the inter-individual differences in MTX disposition in ALL cells, provides new insights into the pharmacogenomics of ALL treatment.

Various publications, patent applications and patents are cited herein, the disclosures of which are incorporated by reference in their entireties.

We claim:

1. A method for predicting the level of gamma glutamyl hydrolase (GGH) activity in a human subject comprising determining the nucleotide present in each GGH allele of the genomic DNA of said subject at a position in exon 5 of human GGH corresponding to position 511 of SEQ ID No. 1, wherein presence of cytosine or thymine nucleotides in the GGH alleles is indicative of the level of GGH activity in the subject.

2. The method of claim 1 wherein the step of determining the nucleotide present in each GGH allele of said subject at the selected position is accomplished by sequencing a region of the genomic DNA of said subject which includes said position.

3. The method of claim 1 wherein the step of determining the nucleotide present in each GGH allele of said subject at the selected position is accomplished by (a) amplifying a portion of the genomic DNA of said subject which includes said position to generate an amplified fragment, and (b) treating the amplified fragment with a restriction enzyme in its corresponding restriction buffer to determine the identity of the nucleotide present at said position.

4. The method of claim 1 wherein the step of determining the nucleotide present in each GGH allele of said subject at the selected position is accomplished by (a) amplifying a region of the genomic DNA of said subject which includes said position, and (b) hybridizing the amplified region with multiple probes that vary only at the nucleotide designed to hybridize to the nucleotide at said position, wherein hybridization determines the identity of the nucleotide present at said position.

* * * * *